United States Patent [19]

Ohsugi et al.

[11] Patent Number: 5,220,591
[45] Date of Patent: Jun. 15, 1993

[54] TOTAL REFLECTION X-RAY FLUORESCENCE APPARATUS

[75] Inventors: Tetsuya Ohsugi; Michihisa Kyoto, both of Yokohama; Kazuo Nishihagi, Neyagawa, all of Japan

[73] Assignees: Sumitomo Electric Industries, Ltd.; Technos Co. Ltd., both of Osaka, Japan

[21] Appl. No.: 813,931

[22] Filed: Dec. 27, 1991

Related U.S. Application Data

[62] Division of Ser. No. 597,027, Oct. 15, 1990.

[30] Foreign Application Priority Data

Oct. 19, 1989 [JP] Japan .................................. 1-272123
Oct. 19, 1989 [JP] Japan .................................. 1-272124

[51] Int. Cl.$^5$ ............................................ G01N 23/223
[52] U.S. Cl. ........................................ 378/45; 378/44; 378/70; 378/79; 378/84
[58] Field of Search ...................... 378/44–46, 378/49, 50, 53, 72, 75, 84, 85, 70, 79

[56] References Cited

U.S. PATENT DOCUMENTS

| | | | |
|---|---|---|---|
| 3,418,466 | 12/1968 | Herglotz | 378/49 |
| 4,121,098 | 10/1978 | Jagoutz et al. | 378/49 |
| 4,169,228 | 9/1979 | Briska et al. | 378/45 |
| 4,349,738 | 9/1982 | Baecklund | 378/49 |
| 4,642,811 | 2/1987 | Georgopoulos | 378/53 |
| 4,649,557 | 3/1987 | Hornstra et al. | 378/84 |
| 4,916,720 | 4/1990 | Yamamoto et al. | 378/81 |
| 5,062,127 | 10/1991 | Sayama et al. | 378/45 |

FOREIGN PATENT DOCUMENTS 0265618 5/1988 European Pat. Off. .
2400704 3/1979 France .

OTHER PUBLICATIONS

A. Iida, et al., "Grazing Incidence X-Ray Fluorescence Analysis," Nuclear Instruments & Methods in Physics Research, Section A, vol. A–246, Nos. 1/3, pp. 736–738, May 1986.

H. Aiginger, et al., "A Method for Quantitative X-Ray Fluorescence Analysis in the Nanogram Region," Nuclear Instruments and Methods vol. 114, pp. 157–158, 1974.

*Primary Examiner*—David P. Porta
*Assistant Examiner*—Kim-Kwok Chu
*Attorney, Agent, or Firm*—Stevens, Davis, Miller & Mosher

[57] ABSTRACT

A total reflection X-ray fluorescence apparatus comprises a base material having an optically flat surface for totally reflecting X-rays radiated at a small glancing angle, a first detector such as an SSD for detecting fluorescent X-rays emerging from a specimen located near the optically flat surface of the base material and a second detector such as a scintillation counter for detecting intensity of X-rays coming from the base material.

17 Claims, 8 Drawing Sheets

AFTER SAMPLING

DOTS INDICATE
ATTACHED PARTICLES

BEFORE SAMPLING

DOTS INDICATE
ATTACHED PARTICLES

DOTS INDICATE
ATTACHED PARTICLES

TOTAL REFLECTION X-RAY FLUORESCENCE APPARATUS

This is a divisional of application Ser. No. 07/597,027 filed Oct. 15, 1990.

BACKGROUND OF THE INVENTION

1. Field of the Invention

The present invention relates to a total reflection X-ray fluorescence apparatus used in a trace analysis of particles located near a surface such as surface contaminations by total reflection X-ray fluorescence.

2. Related Background Art

Total reflection X-ray fluorescence will be briefly described below.

When X-rays are radiated on an optically flat surface at a small glancing angle, the X-rays are reflected at the same angle as the glancing angle without being absorbed by a radiated material. In other words, the X-rays are totally reflected. In this case, if a specimen is placed on the surface by which the X-rays are totally reflected, since X-rays other than those radiated on the specimen are totally reflected, fluorescent X-rays emerging from the specimen can be detected in a state wherein scattered X-rays can be apparently ignored. Therefore, a spectral measurement with a high S/N ratio can be attained (Nippon Kinzoku Gakkai Kaiho, vol. 24, No. 11 (1985) pp. 956-961). Such an analysis method is called the total reflection X-ray fluorescence.

Qualitative/quantitative analysis of the specimen is performed based on the result of the spectral measurement. As analysis examples, for qualitative/quantitative analysis of a specimen placed on a wafer surface, "Progress in X-ray Analysis 19" (Agune Technical Center) pp. 217 $\propto$ 226, Technical Reports of University of Electro-Communications, Osaka, "Natural Science Edition" 22 (1986), from p. 87), and the like are known, and for qualitative/quantitative analysis of a solution dripped on a wafer surface, "Progress in X-ray Analysis 19" (Agune Technical Center)pp. 237-249, and the like are known.

According to the prior art technique, it was difficult to make X-rays radiate at a small glancing angle to the optically flat surface on which a specimen is placed so as to meet conditions in total reflection of X-rays.

Also, if X-rays total reflection conditions are satisfied, X-rays enter to a depth of about 100 Å of a surface portion of an optically flat surface. For this reason, X-rays detected by the above-mentioned total reflection X-ray fluorescence include fluorescent X-rays radiated from a base material having the optically flat surface, and X-rays unique to an X-ray source target (Mo, W, or the like) and continuous X-rays (white X-rays). Since those X-rays are detected as a background level of the analysis result, they induce an increase in detection lower-limit density of a small amount an of element placed as a specimen on the optically flat surface of the base material, and also induce a decrease in quantitative precision of the element.

Further, although the conventional total reflection X-ray fluorescence apparatus, can designate an analysis position on a surface for totally reflecting X-rays, it cannot be discriminated by only analysis of the designated position whether the designated region can represent an attaching state of a particle on the entire surface for totally reflecting X-rays or corresponds to a region where a large amount of particles is locally present. For this reason, the surface for totally reflecting the X-rays is divided into a plurality of regions. The amount of particles cannot be determined unless analysis is independently performed for all the divided regions to confirm an attaching state of a particle, resulting in much time and poor work efficiency.

SUMMARY OF THE INVENTION

It is therefore an object of the present invention to eliminate the above drawbacks.

In order to achieve the above object, an apparatus according to a first aspect of the invention comprises a base material having an optically flat surface for totally reflecting X-rays radiated at a small glancing angle, first detection means for detecting fluorescent X-rays emerging from a specimen located near the optically flat surface of the base material and second detection means for detecting on intensity of an X-rays coming from the base material.

Also, a method according to a aspect of the invention comprises the step of approaching at least one of said optically flat surface and said X-ray beam so that said X-ray beam can coincide with said optically flat surface, holding the positions of said optically flat surface and said X-ray beam just before the intensity of said X-ray beam changes due to the approaching between said optically flat surface and said X-ray beam, inclining said optically flat surface in predetermined angle on an axis intersecting said X-ray beam on said optically flat surface.

Also, an apparatus according to a third aspect of the invention comprises monochromatic means for monochromatizing the X-rays radiated from X-ray source and radiating the monochromatized X-rays onto the optically flat surface at a small glancing angle instead of the second detection means of the apparatus according to the 1st invention.

Further, an apparatus according to a fourth aspect of the invention comprises positioning means for setting coordinates on the optically flat surface and positioning the base material and a surface inspection system for performing state inspection of the optically flat surface and obtaining inspection data of each point on the optically flat surface in correspondence with the coordinates instead of the second detection means of the apparatus according to the 1st invention.

According to the total reflection X-ray fluorescence apparatus of first aspect of invention, since intensity of X-rays can be detected by second detection means, a precise positioning of a base material to X-rays to be radiated thereon is obtained.

According to the method of second aspect of the invention, the positioning of the base method with a predetermined angle can be made easily.

According to the total reflection X-ray fluorescence apparatus of the third aspect of the invention, since only X-rays in a specific wavelength monochromatized by the monochromator means are radiated on the optically flat surface of the base material on which a specimen is placed, unnecessary continuous X-rays are removed from X-rays to be radiated from the base material, and background components in a detected spectrum can be eliminated. Therefore, a small amount of an element can be easily identified, and its quantitative precision can be improved. Further, it is possible to identify a particle attached on the surface, a particle buried in the neighborhood of the surface, and an element of linear material formed perpendicularly to the surface according to the apparatus.

According to the total reflection X-ray fluorescence apparatus of the fourth aspect of the invention, supplemental information necessary for determining an amount of particle on the basis of an analysis result obtained by the total reflection X-ray fluorescence and supplemental information necessary for efficiently performing the total reflection X-rays fluorescence can be obtained by the surface inspection system within a short period of time. Therefore, analysis with high precision can be performed with high work efficiency on the basis of this information.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENT

Figure 1:
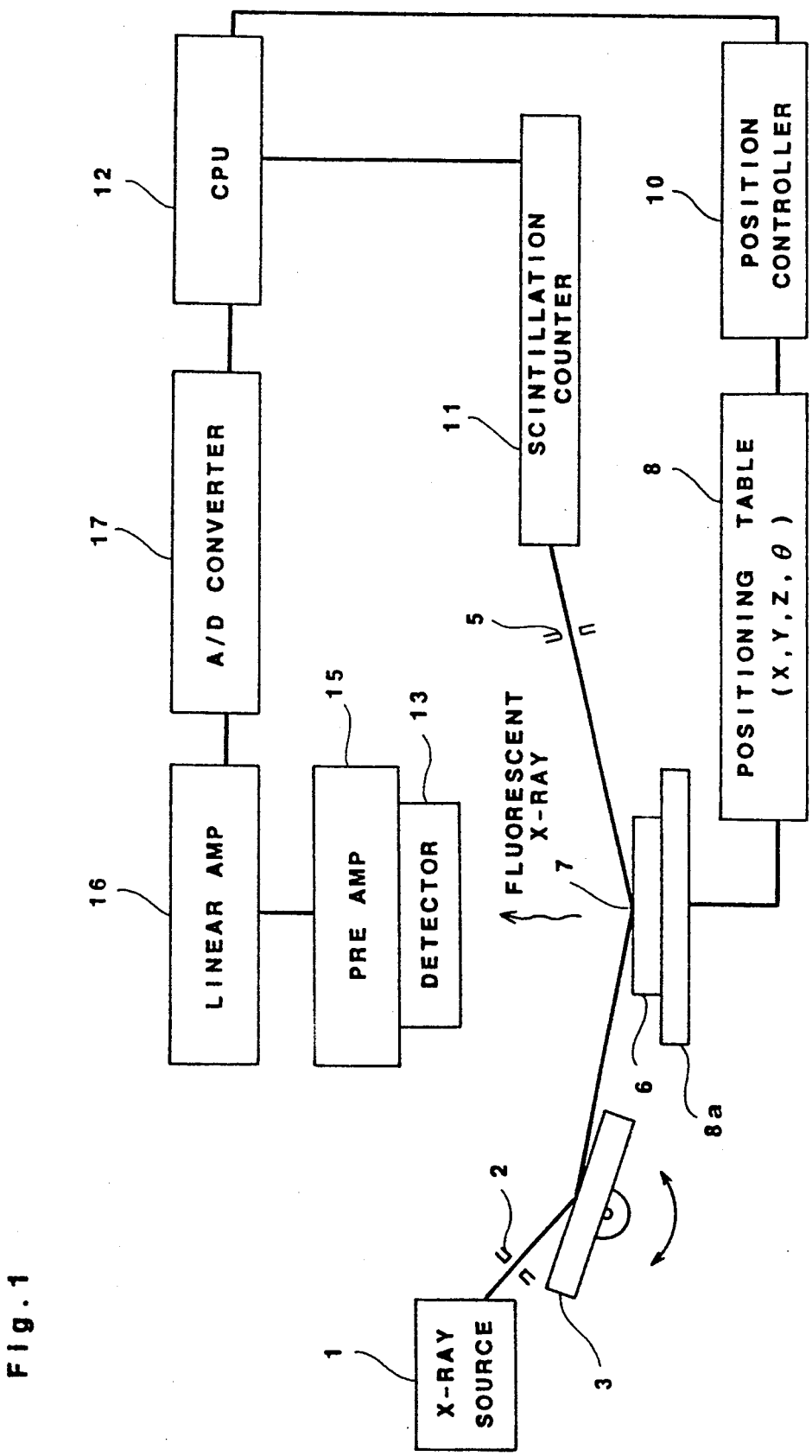
FIG. 1 is a schematic diagram showing a total reflection X-ray fluorescence apparatus according to the present invention.

The first embodiment of the present invention will now be described with reference to FIGS. 1 to 4.

X-rays radiated from an X-ray source such as an X-ray emission tube are converted to a collimated X-ray beam by a slit 2, and the X-ray beam is monochromatized by an monochromator means 3. For X-ray source, a sealed X-ray tube having Mo as its target and an X-ray source having a W tungsten rotating anode target (see FIG. 2) can be used as an exciting source. The latter X-ray source can generate higher power of X-rays than the former X-ray tube since the latter X-ray source uses a rotating target. As the monochromator means 3, a crystal of lithium fluoride (LiF) can be used, and X-rays radiated from the X-ray source 1 are reflected (diffracted) by its crystal plane of (200), thus monochromatizing X-rays. For the monochromator means 3, a crystal of topaz, Si, NaCl, calcite CaCO3, Ge α-quartz, graphite, InSb and pentaerythritol, etc. can be used. The X-rays monochromatized are radiated on an optically flat surface of a base material 6 at a small glancing angle. Note that the monochromator means 3 can change its fixing angle to the glancing angle of X-rays, so that X-ray monochromatized in any wavelength range after the monochromatization can be radiated on the base material 6. Therefore, only X-rays unique to a target used as the X-ray source 1 can be radiated on the base material 6. A specimen 7 is placed on the surface of the base material 6, which surface is irradiated with the X-rays. As the specimen 7 is fixed by an chuck utilizing electrostatic force provided with the base material 6, the warpage of the base material 6 having a specimen 7 thereon is straightened to allow the surface of the specimen 7 to be flat. The base material 6 is placed on a stage 8a of the positioning table 8, and the positioning table 8 is subjected to positioning control by a controller 10.

In this case, the positioning for the specimen 7 may be performed by positioning the monochromator means 3 controlled by controller 10 instead of positioning the positioning table 8.

X-rays reflected by the base material 6 are incident on a scintillation counter 11 via a slit 5. The scintillation counter 11 measures an X-ray intensity. A prior art type of scintillation counter having a phototube can be used for the scintillation counter 11. The measured X-ray intensity is input to a central processing unit 12 comprising, e.g., a CPU. On the basis of this intensity, a table position control instruction is output from the central processing unit 12 to the controller 10 to perform positioning control of the base material 6, thus satisfying X-ray total reflection conditions.

Figure 2A:
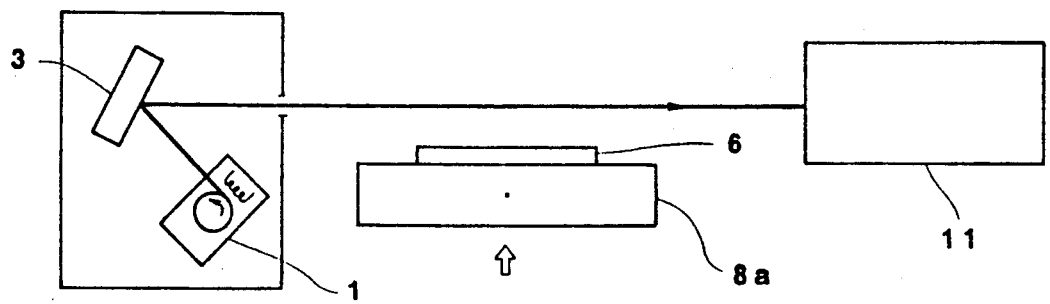
FIGS. 2A to 2C are flow charts showing a method for adjusting glancing angle of X-rays which can be used for the present invention.
Figure 2B:
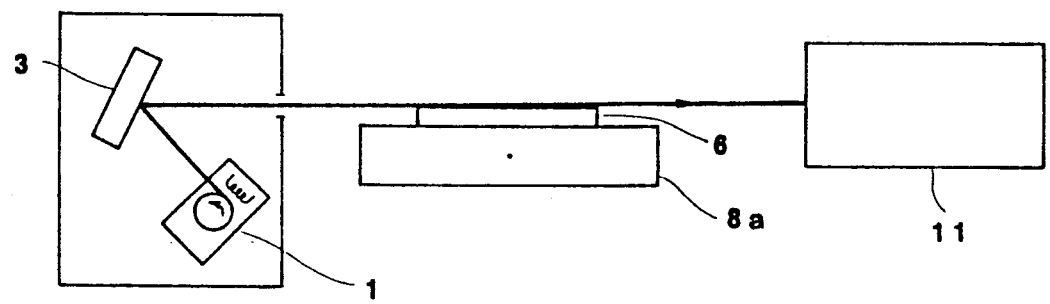
Figure 2C:
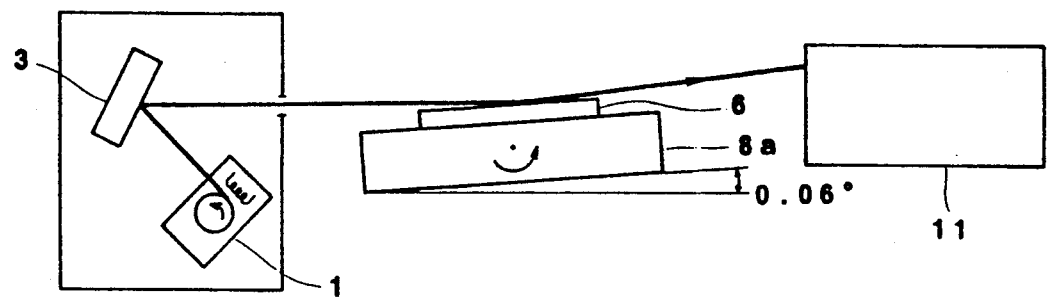

Next, a method for adjusting a glancing angle of X-ray to a base material which can be applied for the present invention is explained which reference with FIGS. 2A to 2C.

The optimized angle of X-rays is about 0.06 degree where the base material 6 having an optically flat surface is a Si wafer for example. The specimen 7 is attached on the optically flat surface of the base material 6. The positioning of the base material 6 is performed as follows.

First, X-rays radiated from an X-ray source are caused to be directly incident into a scintillation counter 11 and an intensity of the X-rays is measured by the scintillation counter 11 (FIG. 2A). After that, the optically flat surface of the base material 6 is coincided with the X-rays so that the X-rays may contact wholly with the optically flat surface (FIG. 2B). If the coincidence between them could not be perfectly made, the intensity of X-rays should be changed due to scattering or absorption of the X-rays. Therefore, it is possible to make a precise coincidence by monitoring the intensity changes. After achieving coincidence, the stage 8a of positioning table 8 is precisely inclined by 0.06 degree on an axis perpendicular to the direction of X-rays radiation on the optically flat surface so as to obtain the glancing angle of 0.06 degree which meets a condition of total reflection for X-rays (FIG. 2C). The critical angle (maximum angle) of $\theta c$ which meets the condition of total reflection can be calculated by the following equation $$\theta_c = \{(5.4 \times 10^{10}) Z \rho / A\}^{1/2} \lambda$$

where Z is an atomic number of the constitutional element. A is the atomic weight and λ the wavelength of the glancing beam. Generally, an optimized angle which varies for different materials and at which a maximum intensity of fluorescent X-rays can be obtained is approximately one third of the critical angle. It is experimentally confirmed by the present inventors that the optimized angle for GaAs is 0.09 degree and that for InP is 0.07 degree for example (Peter Wobrauschek and Hannes Alglnger, Analytical Chemistry, Vol. 44B, No. 5 (1989) 483).

A semiconductor X-ray detector 13 such as a SSD (Solid State Detector) is arranged above the base material 6 to oppose the optically flat surface of the base material 6. The semiconductor X-ray detector 13 utilizes a phenomenon in which X-rays radiated onto a Si diode applied with an inverse voltage results in current flow to generate pulses. Concretely, Si material is doped by Li to form a P-i-n type diode and the P-i-n type diode is applied with an inverse voltage for use. The Si(Li) itself is sealed in a vacuum tube and X-rays are incident thereon through a window made of beryllium foil several microns thick. Since the diode has Li doped therein a certain number of electron-hole pairs corresponding to the energy of X-rays incident on the i-layer of the diode is generated to output pulses. The energy of the X-rays can be detected by measuring the wave height (voltage) and the intensity of the X-rays can be detected by counting the number of pulses.

The SSD published by K. Nishihagi et al in the Extended Abstracts of Electro Chemical Societyt of Vol. 89-2 and the Si(Li) type SSD made of Link Co. Ltd. (detection area: 80 mm$^2$, diameter: 10 mm) may be used for the semiconductor X-ray detector 13. The semiconductor X-ray detector 13 detects fluorescent X-rays radiated from the specimen 7 placed on the base material 6. This detection output is amplified by a preamplifier 15 and a linear amplifier 16, and is extracted as a pulse output having a peak value proportional to the magnitude of a fluorescent X-ray energy. The preamplifier 15 may be directly connected to the semiconductor X-ray detector 13 to prevent the S/N ratio from lowering. Further, the semiconductor X-ray detector 13 and the preamplifier 15 may be cooled by liquid nitrogen in order to reduce thermal noise as much as possible. This pulse output is converted into a digital output by an A/D converter 17, and the digital output is accumulated according to energy by a multichannel analyzer. The accumulated output is then subjected to data processing in the central processing unit 12.

Further, if air exists on the path of fluorescent X-rays between the specimen 7 and the semiconductor X-ray detector 13, the detection intensity is lowered due to scattering and absorption by particulate matter in the air. In this case, as fluorescent X-rays of Ar existed in the air is excited by X-rays, it becomes difficult to detect fluorescent X-rays of Cl and K since their energy values are very close to that of Ar. Accordingly, it is preferable that the chamber in which the fluorescent X-rays are measured is in a vacuum atmosphere. In this case, the degree of vacuum is preferably below 0.1 Torr. For example, a peak energy intensity for Si is 0.1 cps where the degree of vacuum is 760 Torr, but the peak energy intensity increases to 2.2 cps where the degree of vacuum is 0.01 Torr. Since the vacuum atmosphere prevents the energy intensity from lowering, an efficiency for detecting light elements is improved.

Figure 3:
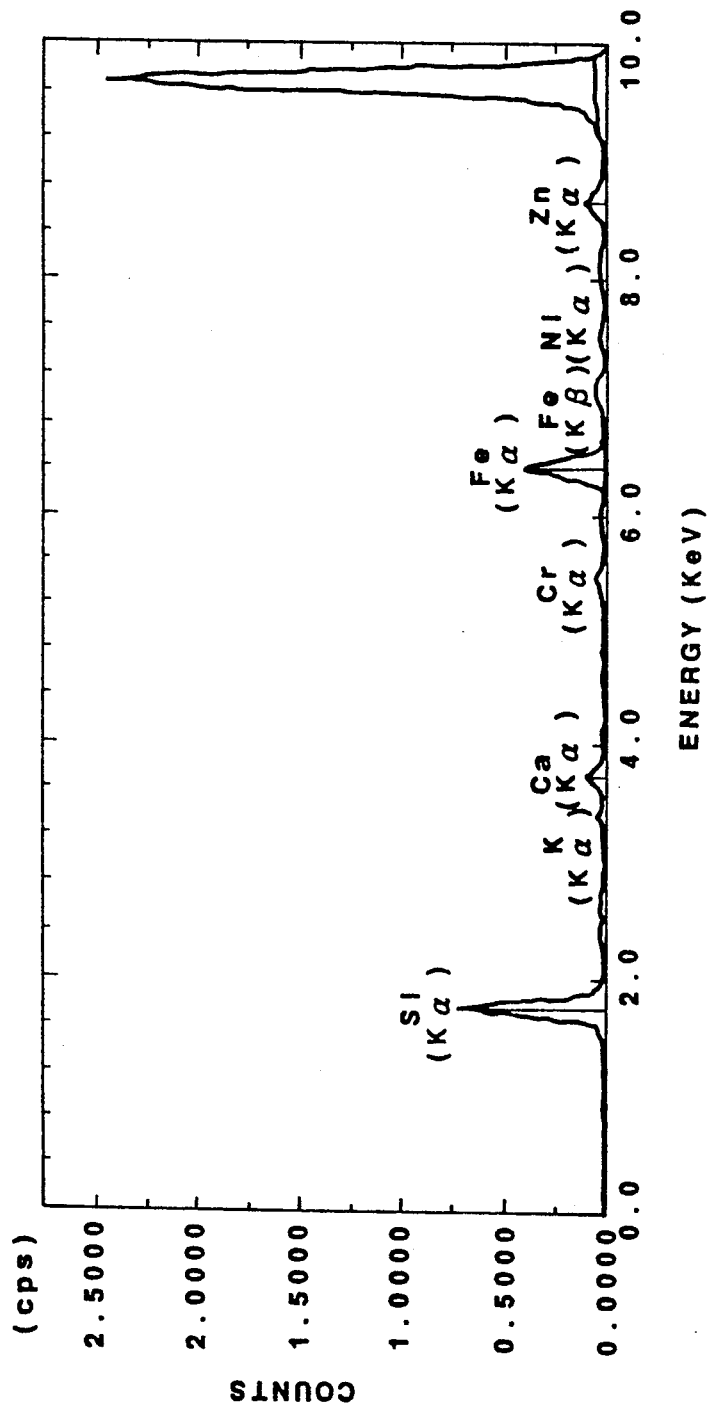
FIG. 3 is a graph showing an analysis result obtained by using the total reflection X-ray fluorescence apparatus according to the present invention.

FIG. 3 shows an analysis result of the above-mentioned total reflection X-ray fluorescent apparatus. This analysis was performed using tungsten (W) for the X-ray source, and a spectral crystal of lithium fluoride (LiF) as the monochromator means, and X-rays were spectrally diffracted by a (200) plane of the spectral crystal. Contamination particles as a specimen became attached onto an optically flat finished surface of a silicon wafer, and were analyzed. Note that this analysis was performed by an energy dispersion type detection method. In FIG. 3, energy values of detected fluorescent X-rays are plotted along the abscissa, and X-ray counts (detection frequency) of the respective energy values are plotted along the ordinate, thus representing an analysis result. Upon evaluation of this analysis result, peaks of the count numbers appear at energy values unique to Si, K, Ca, Cr, Fe, Ni, and Zn, respectively, and almost no continuous X-rays (white X-rays) are detected. Therefore, peaks of these elements can be prevented from being concealed behind a background level caused upon detection of continuous X-rays, and these elements can be easily identified. Since peak areas and corresponding element densities have predetermined correlations, amounts of elements can be determined by performing calibration of a specimen whose density is known.

Figure 4:
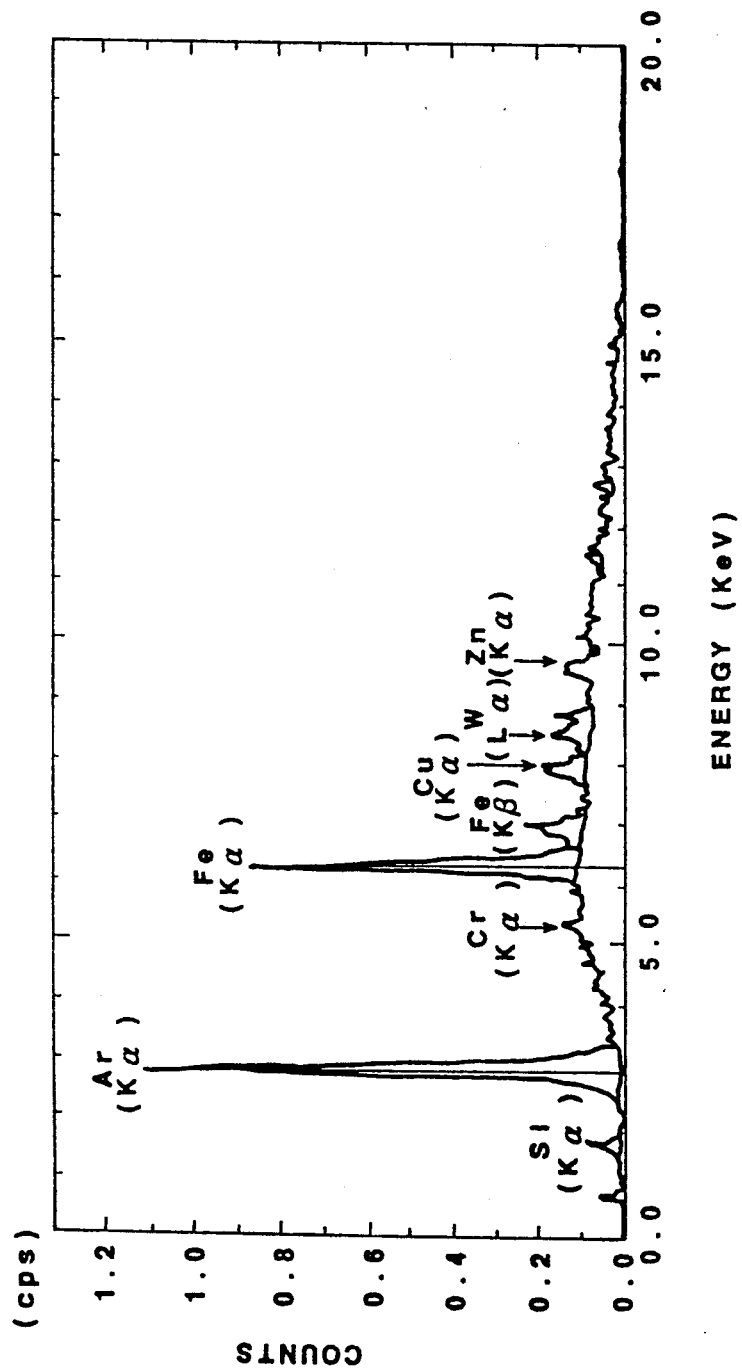
FIG. 4 is a graph showing an analysis result obtained by using a conventional total reflection X-ray fluorescence apparatus.

FIG. 4 shows an analysis result by a conventional total reflection X-ray fluorescent apparatus. In this analysis, molybdenum (Mo) was used for an X-ray source, and X-rays radiated from the X-ray source were radiated on an optically flat surface of a silicon wafer without being monochromatized into monochromatized X-rays. Note that contamination particles attached as a specimen onto the silicon wafer are not the same as those attached in FIG. 3. Upon evaluation of this analysis result, peaks of counts appear at energy values unique to Si, Ar, Cr, Fe, W, and Zn, respectively, and these elements can be identified. However, in this analysis result, since detected X-rays include continuous X-rays, these continuous X-rays are present as a background level of the peak values. For this reason, peaks other than those of Ar and Fe are not easily discriminated from the background level, and peaks may be erroneously judges. When a small amount of element is to be detected, since its peak is concealed behind the background level, a detection lower-limit density of the small amount of element is increased, and the corresponding element cannot often be identified. When a detected element is to be quantitatively measured, a value from which the background level is subtracted must be used as a peak area. However, an error occurs depending on the way of setting the background level, resulting in a decrease in quantitative precision.

In contrast, when the total reflection X-ray fluorescence apparatus according to the present invention is used, only monochrome X-ray components in a specific wavelength range monochromatized by the monochromator means are radiated on the optically flat surface of the base material on which the specimen is placed. Therefore, continuous X-rays are removed from the X-rays radiated from the base material, and can be prevented from being detected by the semiconductor X-ray detector. Therefore, in the obtained analysis result, since the background level caused upon detection of continuous X-rays can be greatly reduced, as shown in FIG. 3, a small amount of an element can be easily identified, and peak areas can be precisely obtained, thus improving quantitative precision.

In the above embodiment, the spectral crystal of lithium fluoride (LiF) is used for the monochromator means. In place of this crystal, a spectral crystal of, e.g., ethylenediamine ditartarate (EDDT), pentaerythritol (PET), or the like, or a diamond type crystal body may be used. In particular, when the diamond type crystal body is used and X-rays are monochromatized by its (111) plane, X-rays in a wavelength range to be extracted can be efficiently monochromatized, and line-spectral monochrome X-ray components with a uniform wavelength can be radiated on the optically flat surface of the base material. Therefore, the above-mentioned identification and quantitative precision can be further improved.

X-rays monochromatized by the monochromator means and radiated on the base material may be any unique X-rays radiated from the X-ray source as long as they have a higher energy than that of an X-ray absorption spectrum of an element to be detected form a specimen. For example, when $K\alpha$ rays as unique X-rays of tungsten (W) are monochromatized by the monochromator means and are radiated on the base material, elements corresponding to atomic numbers below lanthanum (La) are detected since they have a high energy value. However, when $L\beta 1$ rays are monochromatized and radiated on the base material, only elements having atomic numbers equal to or smaller than that of zinc (Zn) are detected. Therefore, elements constituting the base material can be appropriately selected according to X-rays to be radiated so as not to detect a corresponding element. Thus, a background level can be further reduced and analysis precision can be improved. In particular, the present invention is effective for detection of a transition-metal element on a GaAs or InP wafer.

The value of the X-ray fluorescence is and an energy gap between elements is for each element small where the elements have light weights. For example, in case of detecting Na and Mg, the energy value of $K\alpha$ rays for Na if 1.0410 keV and that of $K\alpha$ rays for Mg is 1.2536 keV. Therefore, the energy gap between them is 212.6 eV. In this case, it is impossible to identify peaks if the semiconductor X-ray detector 13 does not have a resolution power to be able to identify the energy gap below 212.6 eV. Accordingly, it is preferable that a semiconductor X-ray detector 13 with resolution power below 200 eV is used for identifying light elements. It is generally known that the energy resolution power of the semiconductor X-ray detector 13 is in proportional to the size of the detecting portion of the semiconductor X-ray detector 13. For example, a semiconductor X-ray detector 13 a with size of 150 mm$^2\phi$ has a resolution power of 250 eV and a semiconductor X-ray detector 13 a with size of 80 mm$^2\phi$ has a resolution power of 150 to 180 eV. Accordingly, it is enough to identify light elements if the size of the detecting portion of the semiconductor X-ray detector 13 is 80 mm$^2\phi$.

The second embodiment of the present invention will be described below with reference to FIGS. 5 to 9.

Figure 5:
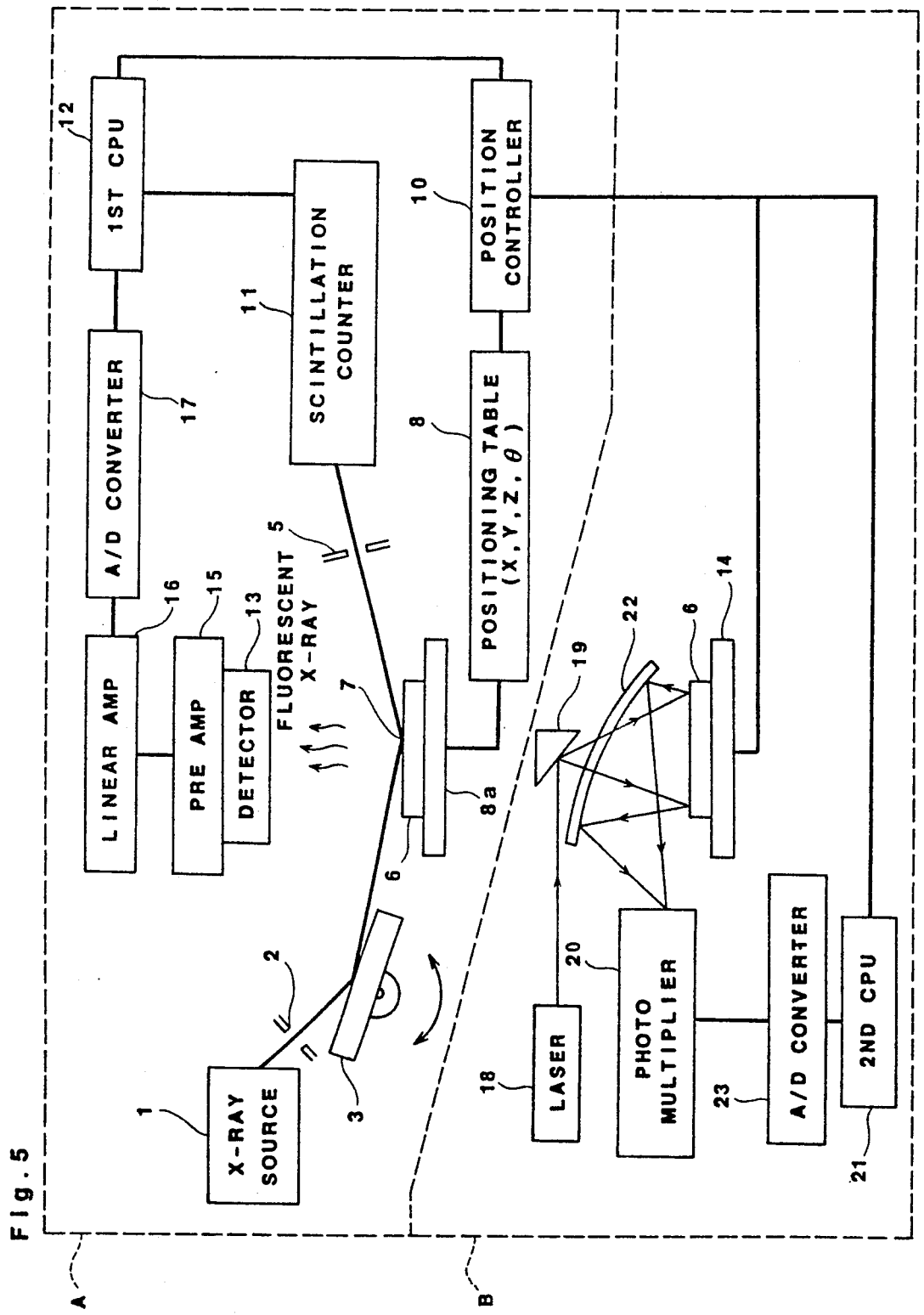
FIG. 5 is a schematic diagram of a total reflection X-ray fluorescence apparatus according to the present invention.

The apparatus illustrated in FIG. 5 can be mainly constituted by an X-ray analysis system A for performing a total reflection X-ray fluorescence, and a surface inspection system B for inspecting a state of a surface where the total reflection X-ray fluorescence is performed. In the X-ray analysis system A, X-rays are radiated from an X-ray source 1 such as an X-ray emission tube, and are collimated to a fine X-ray beam by a slit 2 as described before. The X-ray beam is radiated on an optically flat surface of a base material 6 at a small glancing angle after monochromatization by the monochromator means 3 fixed with a member inclinable to the X-rays. The base material 6 is, for example, a silicon wafer, and a specimen 7 is attached to a surface of the base material 6 where X-rays are radiated. The base material 6 is placed on a stage 8a of a positioning table 8, and is positioned by the positioning table 8. The positioning table 8 has a predetermined coordinate system (x, y, z), and is subjected to positioning control by a position controller 10 according to the coordinate system, Therefore, when the base material 6 is placed on the stage 8a, a coordinate system is set on the optically flat surface of the base material 6 for totally reflecting X-rays.

X-rays radiated on the surface for totally reflecting X-rays (total reflection surface) of the base material 6 are reflected by the surface, and are incident on a scintillation counter 11 via a slit 5. The scintillation counter 11 measures an X-ray intensity. The scattered X-ray intensity is input to a first central processing unit 12 comprising a CPU, a ROM, a RAM, and the like, and a stage position control instruction is output based on the input intensity. The base material 6 is positioned on the basis of the control instruction to satisfy X-ray total reflection conditions. On the total reflection surface of the base material 6, elementary analysis of a particle by the total reflection X-ray fluorescence is performed for a position (region) according to the control instruction. Information associated with a coordinate position corresponding to the control instruction at that time is stored in the RAM of the first central processing unit 12.

A semiconductor X-ray detector 13 such as a SSD (Solid State Detector) is arranged above the base material 6 to oppose the optically flat surface (total reflection surface of the base material 6. The semiconductor X-ray detector 13 detects fluorescent X-rays radiated from a specimen 7 attached onto the base material 6. The detection output is amplified by a preamplifier 15 and a linear amplifier 16, and is extracted as a pulse output having a peak value proportional to a magnitude of the fluorescent X-ray energy. The pulse output is converted into a digital output by an A/D converter 17. The digital output is accumulated by a multichannel analyzer, and is then subjected to data processing in the first central processing unit 12.

The total reflection X-ray fluorescence apparatus according to the present invention has the surface inspection system B for performing surface inspection of the total reflection surface such as an attaching condition of the specimen 7 to the total reflection surface of the base material 6, a distribution and particle size of attached specimen particles, scratches or defects on the total reflection surface, and the like. The surface inspection system B obtains inspection information regarding each point on the total reflection surface in correspondence with coordinates set on the surface of the base material 6, and can store the information. The surface inspection system B comprises a stage 14 on which the base material 6 is placed, a laser 18 for radiating a laser beam to be radiated on the base material 6 placed on the stage, a reflection mirror 19 for reflecting the laser beam to radiate it on the base material 6, a photomultiplier 20 for detecting a reflection light intensity of the laser beam reflected by the base material 6, and a second central processing unit 21 for receiving an output signal digitized by A/D converter 17 from the photomultiplier 20. The reflection mirror 19 changes its position to be able to scan the laser beam on the entire total reflection surface of the base material 6. The laser beam radiated onto the base material 6 is reflected by the base material 6. If foreign matter is present on the base material 6 or in the neighborhood of the surface, the laser beam is scattered by the foreign matter, and an intensity of reflected light is changed. Therefore, information such as a distribution condition if the specimen 7 attached to the total reflection surface can be obtained based on the change in reflected light intensity. The reflected light if focused by an elliptic reflection mirror 22, and is incident on the photomultiplier 20. The light incident on the photomultiplier 20 is converted into an electrical signal according to its intensity, and the electrical signal is amplified and output. The output signal from the photomultiplier 20 is converted into digital data by an A/D converter 23, and is input to the second central processing unit 21. The signal input to the second central processing unit 21 is processed in correspondence with the coordinates set on the total reflection surface, and the processed signal is stored as inspection information such as a distribution condition, particle size, and the number of particles of the specimen 7 attached to the total reflection surface, the number of particles of the specimen present in a region subjected to the total reflection X-ray fluorescence, a ratio of the number of particles to a total number of particles of the specimen attached to the entire total reflection surface, scratches or defects on the total reflection surface, and the like. The surface inspection system B is connected to the X-ray analysis system A via the position controller 10, as shown in FIG. 5. Note that as the surface inspection system B, a surfscan 4500 available from TENCOR INSTRUMENTS can be used.

As described above, in the total reflection X-ray fluorescence apparatus of the present invention with the surface inspection system B, the base material 6 is placed on the stage 14 to perform surface inspection of the total reflection surface of the base material 6 before or after X-ray analysis is performed for the base material 6 placed on the stage 8a. Therefore, in order to discriminate whether a region on the base material 6 where the total reflection X-ray fluorescence is performed represents an attaching state of a particle on the entire total refection surface or corresponds to a region where a large amount of particle is locally present, no time-consuming operation for dividing the total reflection surface into a plurality of regions and independently performing total reflection X-ray fluorescence on all the divided regions to confirm an attaching state and the like of a specimen is required unlike in the conventional apparatus. A coordinate region most suitable for performing the X-ray fluorescence can be searched from the inspection result by the surface inspection system B, and efficient X-ray analysis can be performed. For example, when the total reflection X-ray fluorescence is to be performed for a portion having a highest distribution density of the specimen 7, a region having a highest distribution density is searched from the inspection result of the surface inspection system B, and the X-ray analysis can be performed for only this region. After the total reflection X-ray fluorescence is performed, whether the region on the base material 6 subjected to the fluorescence represents an attaching state of a particle on the entire total reflection surface or corresponds to a region where a large amount of particle is locally present can be easily discriminated. Furthermore, since a ratio of a specimen attached to a portion subjected to the analysis to the entire specimen can be obtained based on the inspection result of the surface inspection system B, the amount of the specimen 7 can be easily determined with high precision using this ratio.

In the total reflection X-ray fluorescence apparatus according to the present invention with the surface inspection system B, as described above, since the X-ray analysis and the surface inspection can be performed as a series of operations, opportunity for foreign matter to become additionally attached to the base material can be reduced, and analysis with higher precision can be performed.

Figure 6A:
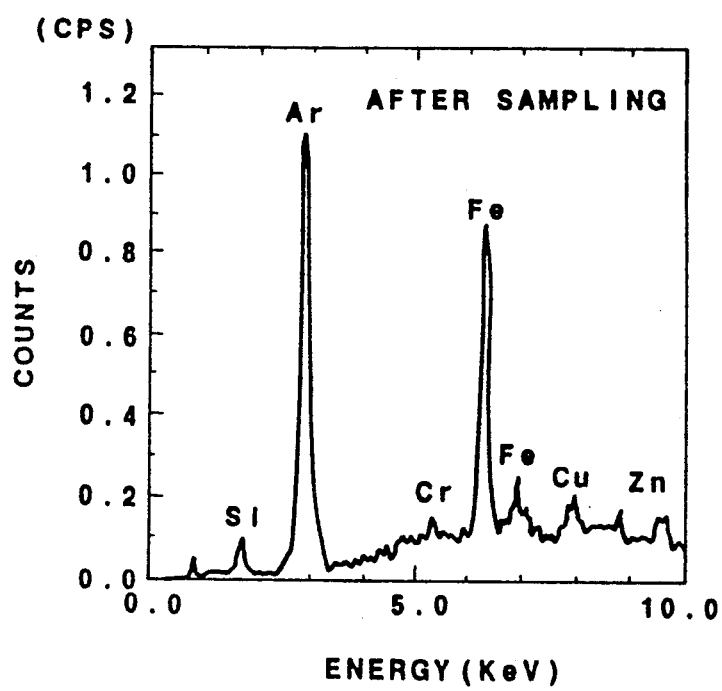
FIGS. 6A and 6B are views showing analysis result by the total reflection X-ray fluorescence apparatus according to the present invention.
Figure 6B:
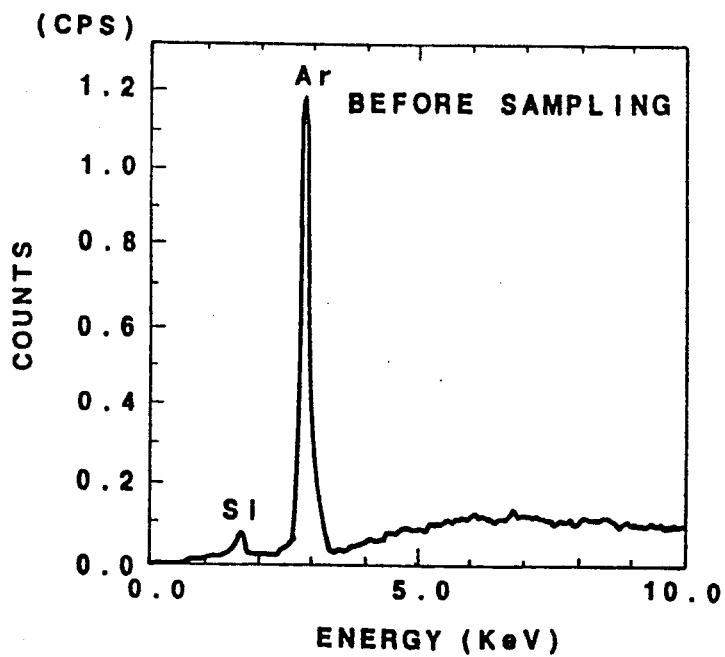

FIGS. 6A and 6B show analysis results of the X-ray analysis system A described above, and FIGS. 7A and 7B show inspection results of the surface inspection system B. FIG. 6A shows an analysis result of the total reflection X-ray fluorescence as follows. That is, $N_2$ gas was sampled from a pipe for introducing $N_2$ gas to, e.g., a semiconductor manufacturing device. The sampled $N_2$ gas was blown on a silicon wafer used as the base material for two hours to specimen contamination particles included in the $N_2$ gas as a specimen, and the total reflection X-ray fluorescence was performed for the contamination particles. FIG. 6B shows an analysis result for the silicon wafer surface before the $N_2$ gas is blown to attach the contamination particles. In these figures, energy values of fluorescent X-rays are plotted along the abscissa, and X-ray counts (detection frequency) of the respective energy values are plotted along the ordinate. Note that this analysis was performed by an energy dispersion type detection method.

Upon examination of this analysis result, peaks appear at energy values unique to Cr, Fe, Cu, and Zn, and corresponding metal elements are identified by them. Upon comparison with the analysis result shown in FIG. 6B, it can be determined that these metal elements are contained in the $N_2$ gas. Since these elements constitute elements of stainless steel and brass, it can be estimated that contamination sources of the $N_2$ gas are pipes and their joints. Since the axis of ordinate represents the counts, a peak area for each element reflects a corresponding element density, and the amount of the element can be determined by performing calibration using a specimen whose density is known.

Figure 7A:
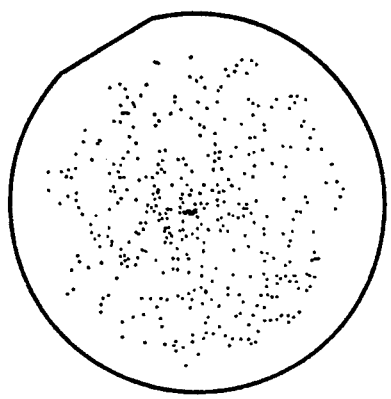
FIGS. 7A, 7B and FIG. 8 are views showing inspection results by a surface inspection system according to the present invention.
Figure 7B:
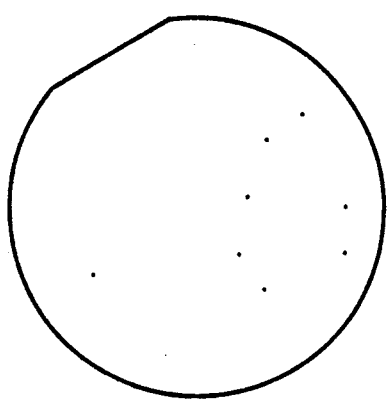

FIG. 7A shows an inspection result of a distribution condition of contamination particles attached to the surface of the above-mentioned silicon wafer after the $N_2$ gas is blown, using the surface inspection system A, and FIG. 7B shows an inspection result of the silicon wafer surface before the $N_2$ gas was blown. As can be seen from these inspection results, a very small amount of contamination particles are attached to the silicon wafer surface before the $N_2$ gas is blown, but a large amount of contamination particles are uniformly distributed and attached to the surface of the silicon wafer after the $N_2$ gas is blown. These results can demonstrate that these contamination elements are particles containing the metal elements identified in FIGS. 6A and 6B.

The analysis position in FIG. 6A corresponds to an area having a diameter of 6 mm at the central portion of the wafer, and it can be determined based on the inspection result of the surface inspection system B that the number of contamination particles attached to that portion is about 10% of the total number of contamination particles. Therefore, it attaching efficiency of the contamination particles can be detected, a density of each element contained in the $N_2$ gas can be calculated based on a peak area of the corresponding element and the total amount of blown $N_2$ gas.

Figure 8:
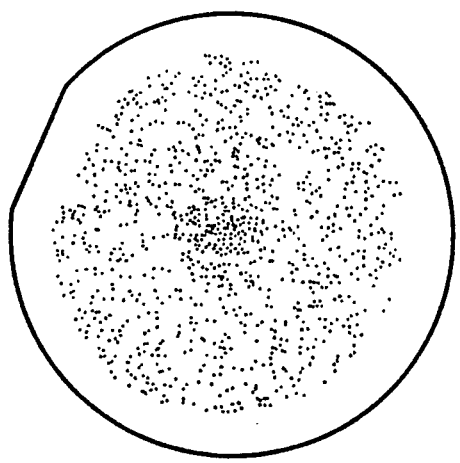

FIG. 8 shows another inspection result of the surface inspection system B, which is different from that in FIGS. 7A and 7B. This inspection result was obtained as follows. That is, a magnet was attached to the central portion of the lower surface of the silicon wafer, and the $N_2$ gas was similarly blown on the upper surface. As can be seen from FIG. 8, since the magnet is attached, contamination particles are concentrated around the magnet. Contamination particles about 20% of the overall contamination particles are attached to an area having a diameter of 6 mm at the central portion of the wafer. Therefore, coordinates of the area where the contamination particles are concentrated and attached are read out, and the positioning table 8 is controlled by the position controller 10 so that the total reflection X-ray fluorescence is performed for this area. When the total reflection X-ray fluorescence is then performed, an analysis result having larger peak values than those in the analysis result shown in FIG. 6A can be obtained, and contamination elements can be detected with high sensitivity. Also precision of quantitative analysis can also be improved.

Figure 9:
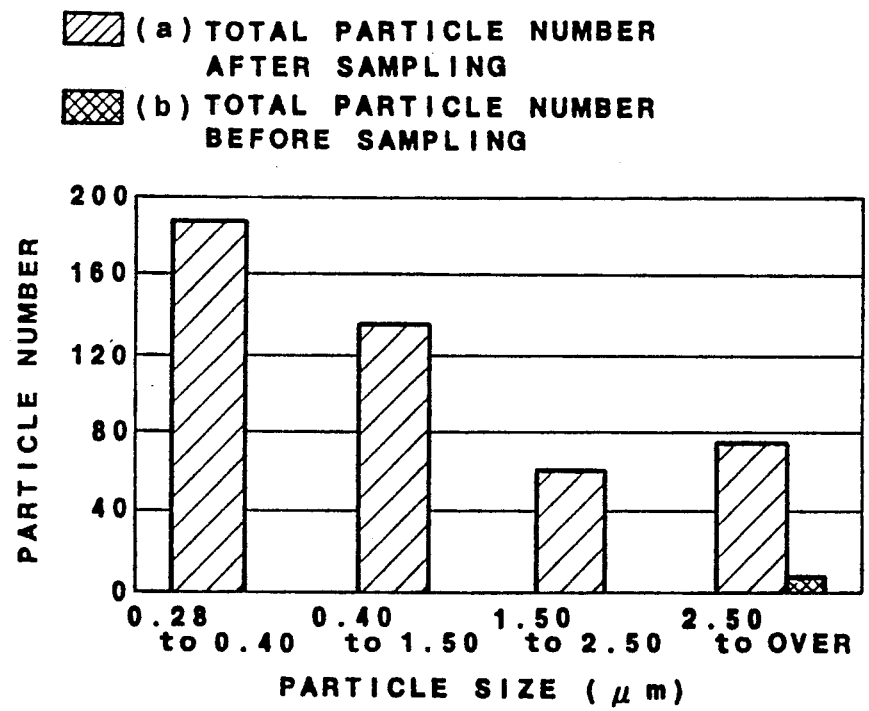
FIG. 9 is a view showing an inspection result by the surface inspection system according to the present invention, which result is different from that shown in FIG. 8.

Note that the surface inspection system B can detect the total number of contamination particles attached to the wafer or the number of particles in units of particle sizes. FIG. 9 shows these detection results. The particles sizes of contamination particles can be an important clue to clear up the cause of contamination.

In the above embodiment, the stage 8a used for the total reflection X-ray fluorescence and the stage 14 used for surface inspection of the total reflection surface are independently arranged, and the base material 6 is transferred between these two stages. Therefore, when the base material 6 is transferred, the base material 6 is preferably transferred in parallel without changing its orientation so that the coordinates set on the total reflection surface during the total reflection X-ray fluorescence can be directly used in surface inspection of the total reflection surface. That is, the relative positional relationship between the X-ray analysis system A and the base material 6 is the same as the positional relationship between the surface inspection system B and the base material 6. Even when different coordinates are set for the X-ray analysis and surface inspection, a coordinate setting reference need only be provided to the base material 6, so that the different coordinates can be converted based on the reference as if common coordinates were set. As the reference, when a semiconductor wafer is used as the base material 6, an orientation flat can be used.

Alternatively, the surface inspection system B may be added to the X-ray analysis system A to have one common stage, so that coordinates common to the X-ray analysis and surface inspection can be set. In this case, a transfer process of the base material 6 can be omitted, and additional attachment of a contamination material on the base material 6 during transfer can be avoided.

Further, although the surface inspection system B uses a laser 18 and a photomultiplier 20 to make an inspection by scanning a laser beam from laser 18 two-dimensionally, a CCD instead of the photomultiplier 20 may be used to make an inspection by linear scanning with laser beams enlarged in certain direction and radiated onto the CCD.

Additionally, a lamp instead of the laser 18 and a CRT instead of the photomultiplier 20 may be used to make an inspection based on image data obtained by CRT.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

We claim:

1. A method for adjusting a glancing angle of an X-ray beam to be radiated onto an optically flat surface, comprising the steps of:

providing a base material having an optically flat surface;

radiating an X-ray beam;

positionally adjusting at least one of said optically flat surface and said X-ray beam so that said X-ray beam is parallel to and coincides with said optically flat surface, whereby said X-ray beam is adapted to be radiated directly into a scintillation counter;

maintaining relative positions of said optically flat surface and said X-ray beam just before an intensity of said X-ray beam changes due to adjustment of relative positions between said optically flat surface and said X-ray beam; and inclining said optically flat surface at a predetermined angle on an axis intersecting said X-ray beam on said optically flat surface.

2. A total reflecting X-ray fluorescence apparatus comprising:

a base material having an optically flat surface for totally reflecting X-rays radiated at a small glancing angle;

detection means for detecting fluorescent X-rays emerging from a specimen located near the optically flat surface of said base material;

positioning means for setting coordinates on the optically flat surface and positioning said base material; and surface inspection system for performing state inspection of the optically flat surface and obtaining inspection data of each point on the optically flat surface in correspondence with the coordinates.

3. An apparatus according to claim 2, further comprising control means for controlling said positioning means on the basis of a scattered X-ray intensity of X-rays reflected by said base material, and satisfying total reflection conditions of the X-rays with respect to said base material.

4. An apparatus as in claim 2, wherein said detection means comprises a semiconductor X-ray detector.

5. An apparatus as in claim 2, further comprising an X-ray source for radiating X-rays and a monochromator means for monochromatizing X-rays radiated from said X-ray source and radiating the monochromatized X-rays onto said optically flat surface at said small glancing angle.

6. An apparatus as in claim 5, wherein said X-ray source comprises a rotating cathode type X-ray source.

7. An apparatus as in claim 5, wherein said monochromator means use a diamond type crystal body, and the X-rays radiated from said X-ray source are reflected by a crystal surface thereof.

8. An apparatus as in claim 5, wherein said monochromator means use a crystal of lithium fluoride (LIF), and the X-rays radiated from said X-ray source are reflected by the crystal surface thereof.

9. An apparatus as in claim 5, wherein said monochromator means use a crystal of ethylenediamine ditartarate (EDDT), and the X-rays radiated from said X-ray source are reflected by the crystal surface thereof.

10. An apparatus as in claim 5, wherein said monochromator means use a crystal of pentaerythritol (PET), and the X-rays radiated from said X-ray source are reflected by the crystal surface thereof.

11. An apparatus as in claim 5, wherein said monochromator means are supported on a support member for changing a fixing angle of said monochromator means so as to radiate said X-rays onto said base material in any wavelength range after the monochromatization.

12. An apparatus as in claim 5, wherein said monochromator means radiate monochrome X-rays having a higher energy than that of an X-ray absorption spectrum of an element to be detected from said specimen onto the optically flat surface.

13. An apparatus as in claim 5, wherein said X-ray source uses tungsten, and said monochromator means use a crystal of lithium fluoride (LIF).

14. A total reflecting X-ray fluorescence apparatus comprising:

a base material having an optically flat surface for totally reflecting X-rays radiated at a small glancing angle;

detection means for detecting fluorescent X-rays emerging from a specimen located near the optically flat surface of said base material;

positioning means for setting coordinates on the optically flat surface and positioning said base material; and surface inspection system for performing state inspection of the optically flat surface and obtaining inspection data of each point on the optically flat surface in correspondence with said coordinates, wherein said surface inspection means comprises a laser scanner for radiating and scanning a laser beam onto said base material, and reflected light detection means for detecting a reflected light intensity of the laser beam reflected by said base material.

15. An apparatus according to claim 14, wherein said laser scanner comprises a laser oscillator for radiating the laser beam, and a reflection mirrors for reflecting and scanning the laser beam toward said base material.

16. An apparatus according to claim 14, wherein said reflected light detection means comprise a photomultiplier.

17. An apparatus as in claim 14, wherein said reflected light detection means comprises a scintillation counter.

* * * * *